United States Patent [19]

Streck

[11] Patent Number: 5,486,164
[45] Date of Patent: Jan. 23, 1996

[54] PASSIVE PROTECTOR FOR HYPODERMIC NEEDLES

[75] Inventor: Donald A. Streck, Kailua, Hi.

[73] Assignee: Showa Hatsumei Kaisha, Ltd., Kailua, Hi.

[21] Appl. No.: 57,514

[22] Filed: May 6, 1993

[51] Int. Cl.⁶ .................................................. A61M 5/32
[52] U.S. Cl. ............................................ 604/198; 604/263
[58] Field of Search ................................. 604/110, 187, 604/192, 195, 198, 263

[56] References Cited

U.S. PATENT DOCUMENTS 5,026,353  6/1991  Bartman ............................ 604/192

Primary Examiner—John D. Yasko
Attorney, Agent, or Firm—Donald A. Streck

[57] ABSTRACT

Apparatus for providing passive protection against accidental needle-stick for a hypodermic needle extending from a hub. There is a tip protector comprising a cross-piece disposed transverse to the needle having an elongated first bore therethrough through which the needle passes and having a bell-shaped tip-guard extending from the cross-piece concentrically about the first bore and covering a tip portion of the needle with the tip protector in an extended position. The tip protector is slidably moveable along the needle supported by the elongated first bore between the extended position and a retracted position with the tip portion of the needle exposed for use. Guide apparatus guides the tip protector between the extended position and the retracted position. A coil spring biases the tip protector to the extended position. A releasable lock automatically and releasably locks the tip protector in the extended position when the tip protector moves to the extended position from a position retracted therefrom. The tip protector can ride on guide rails extending from hub parallel to the needle of on support rails extending from the cross-piece into guide tubes extending from hub parallel to the needle by away from it.

8 Claims, 9 Drawing Sheets

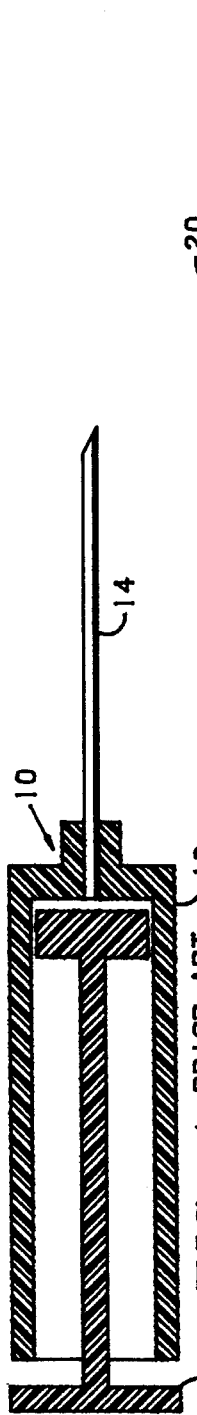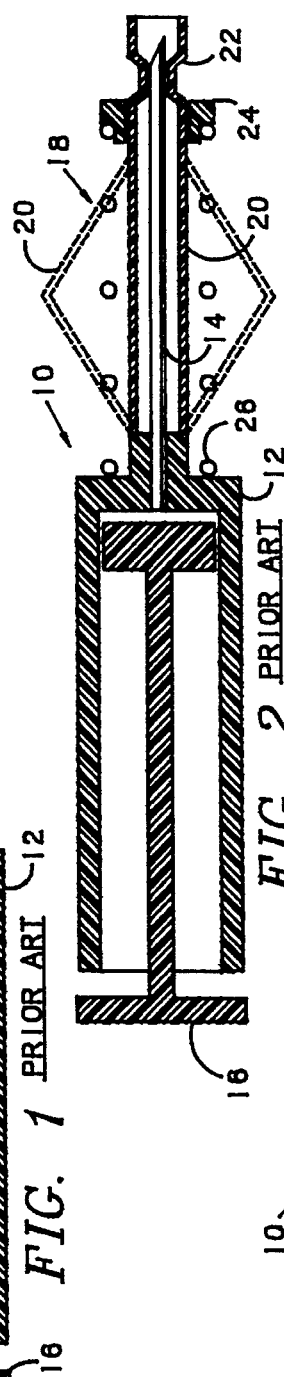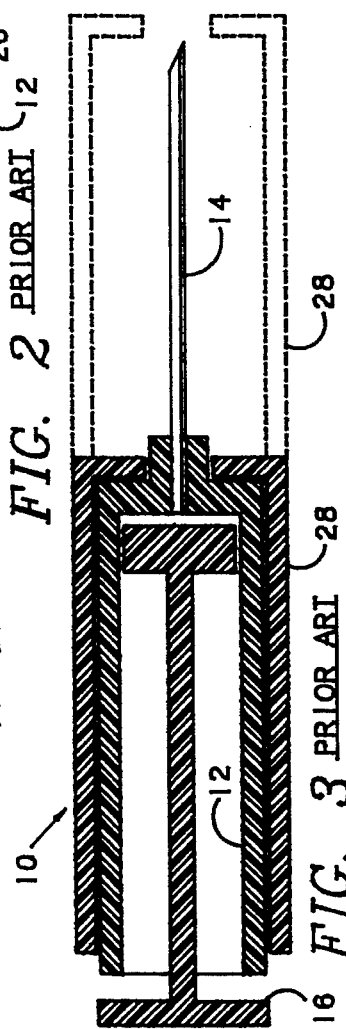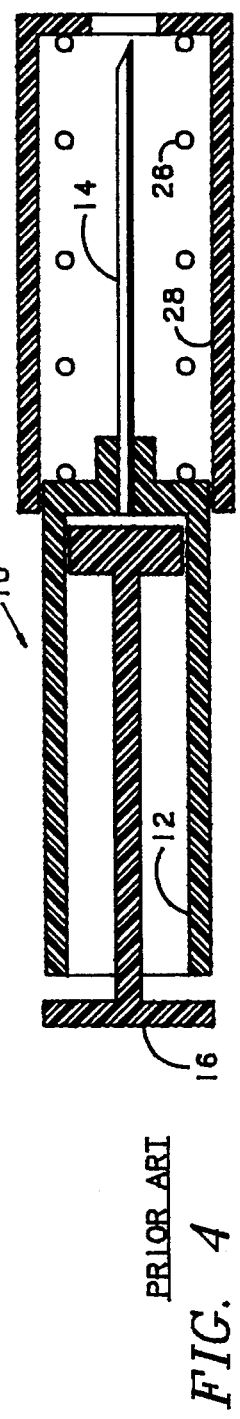
FIG. 1 PRIOR ART
FIG. 2 PRIOR ART
FIG. 3 PRIOR ART
FIG. 4 PRIOR ART

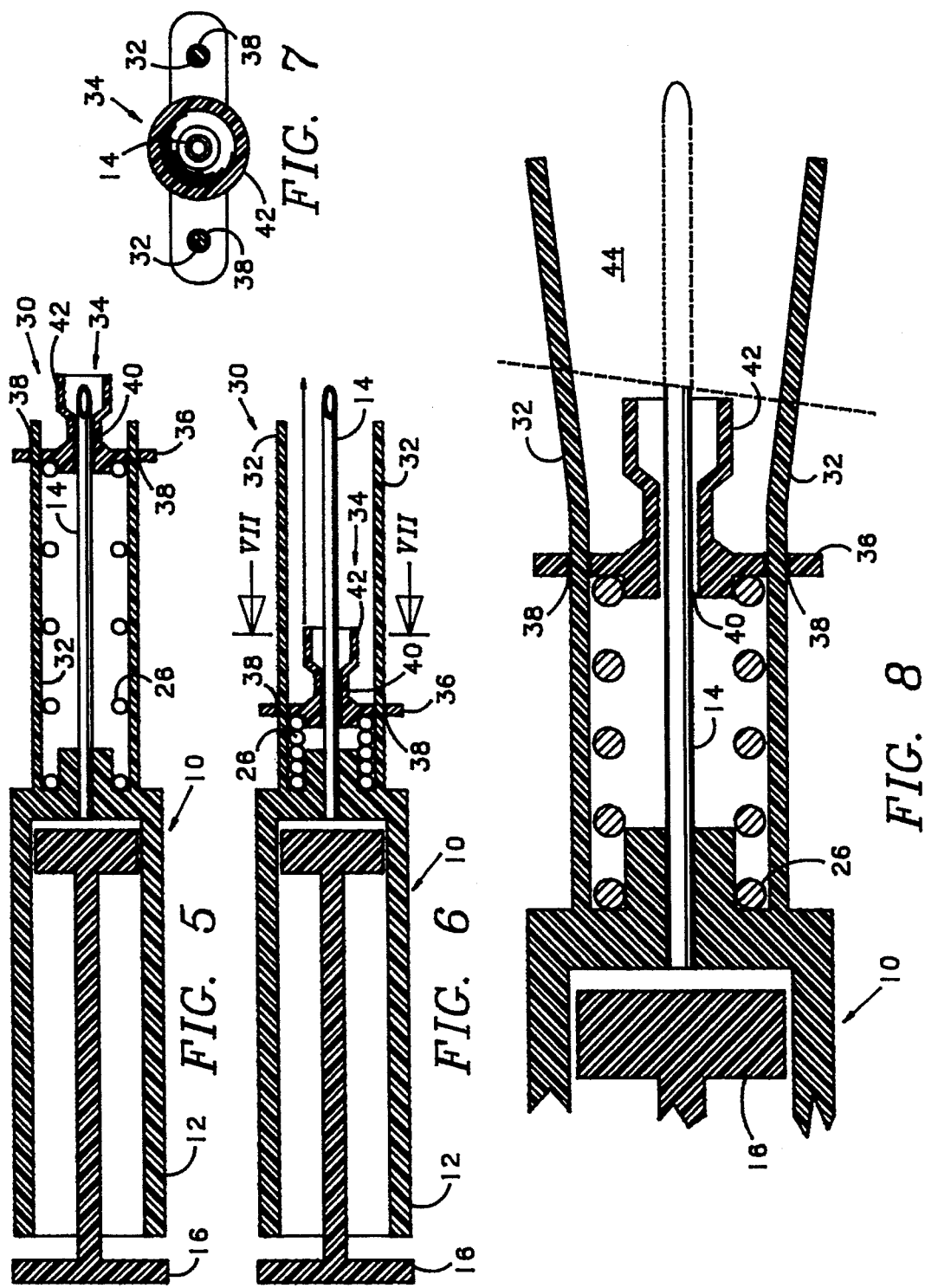

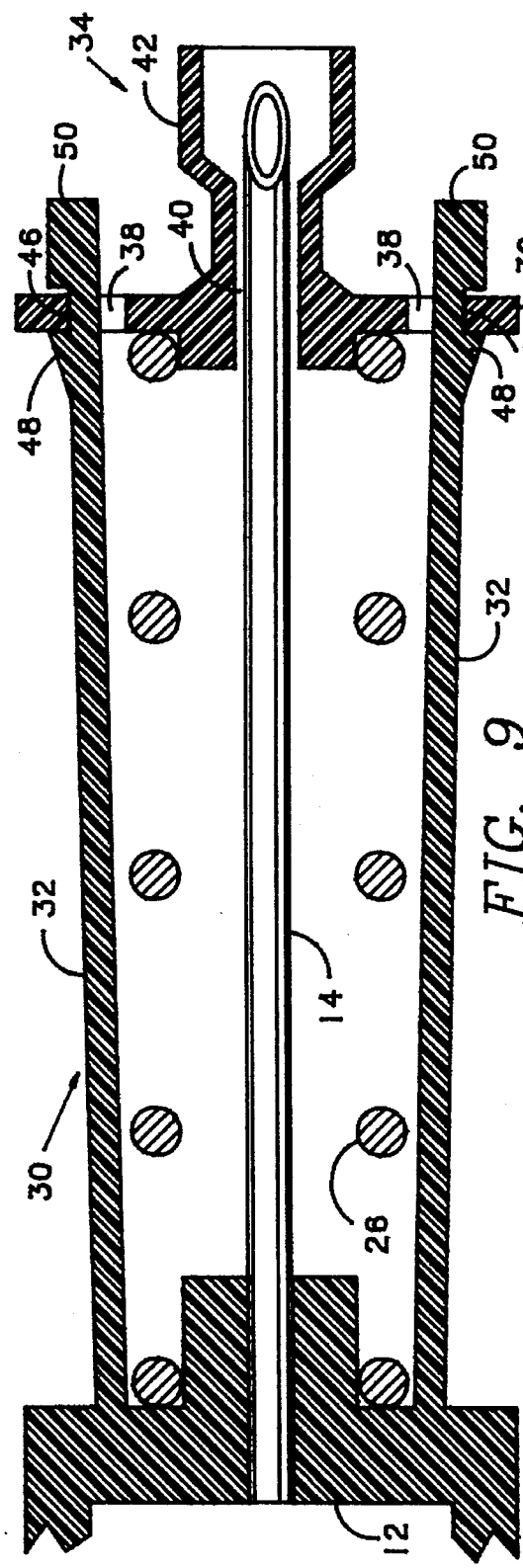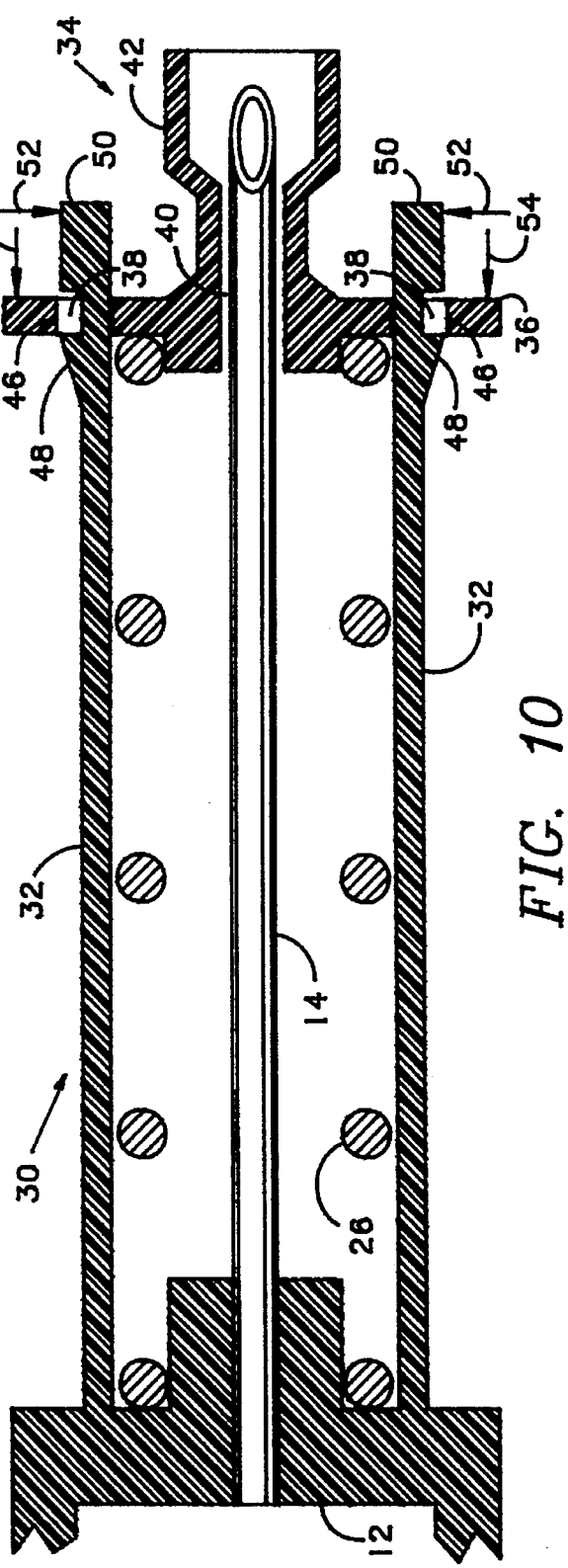

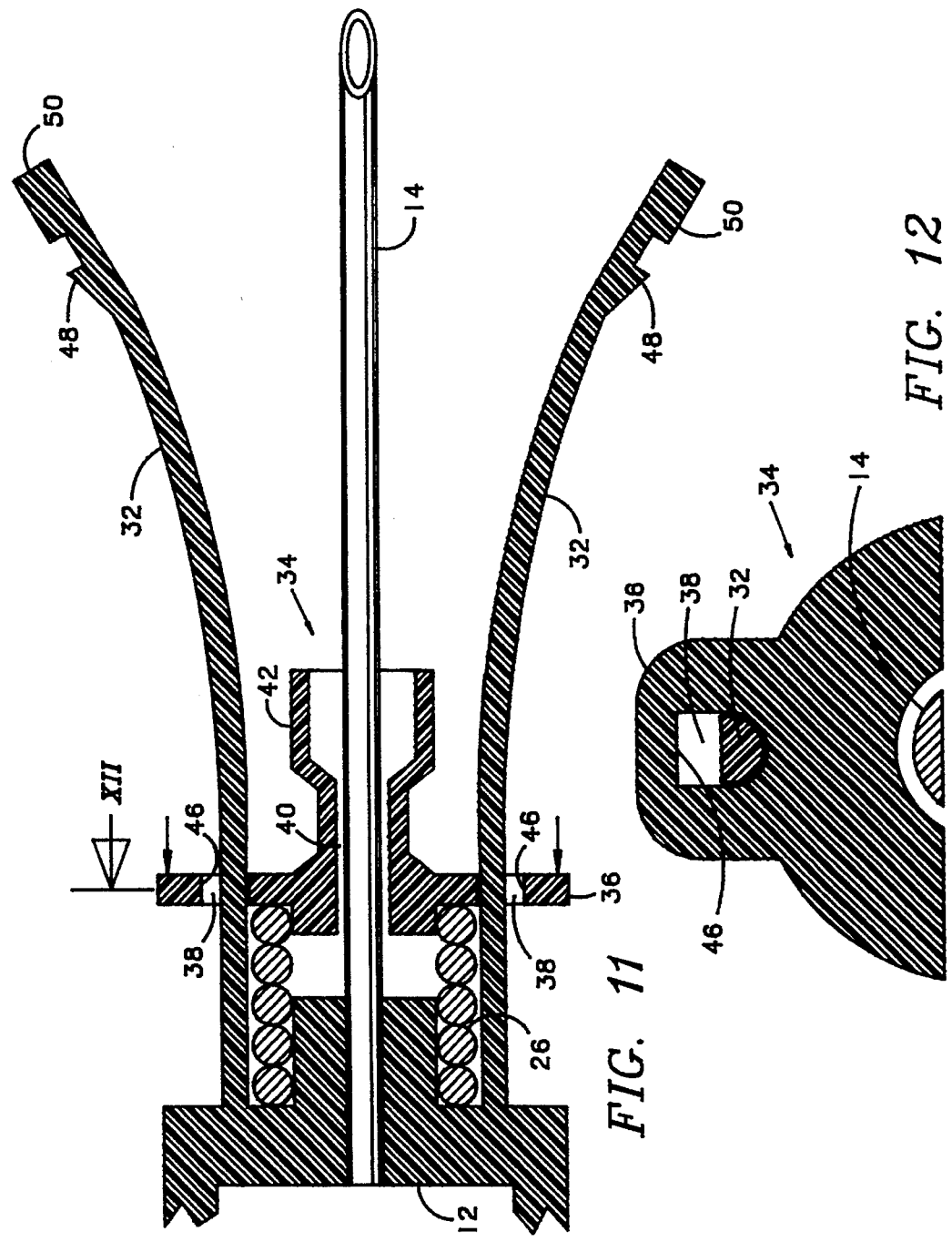

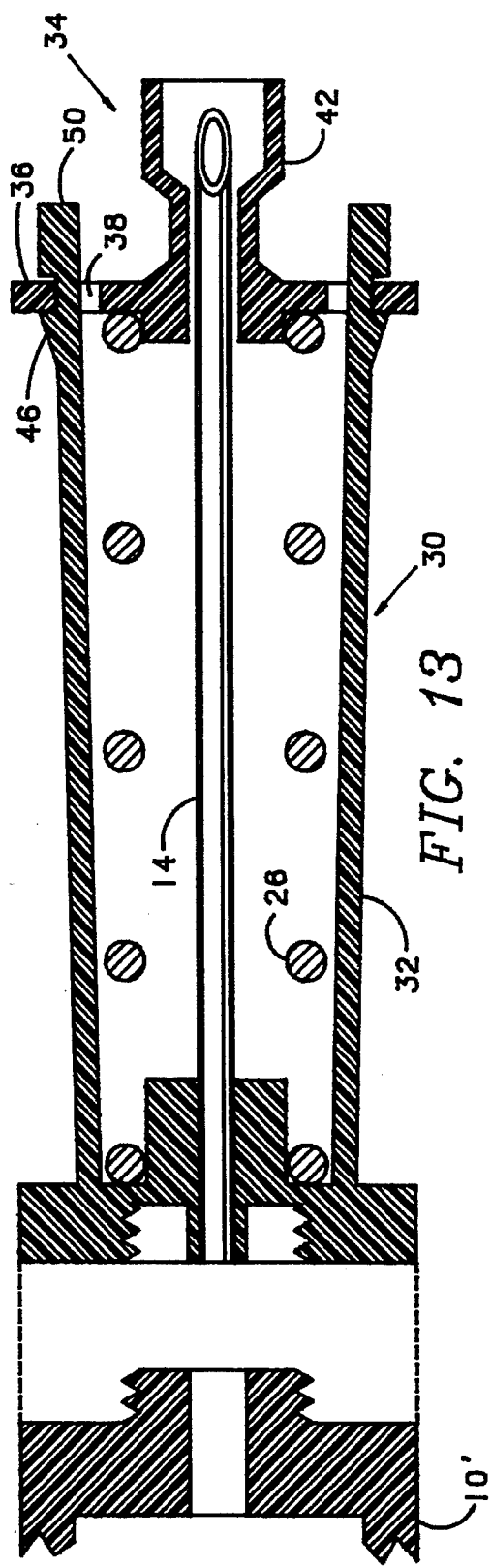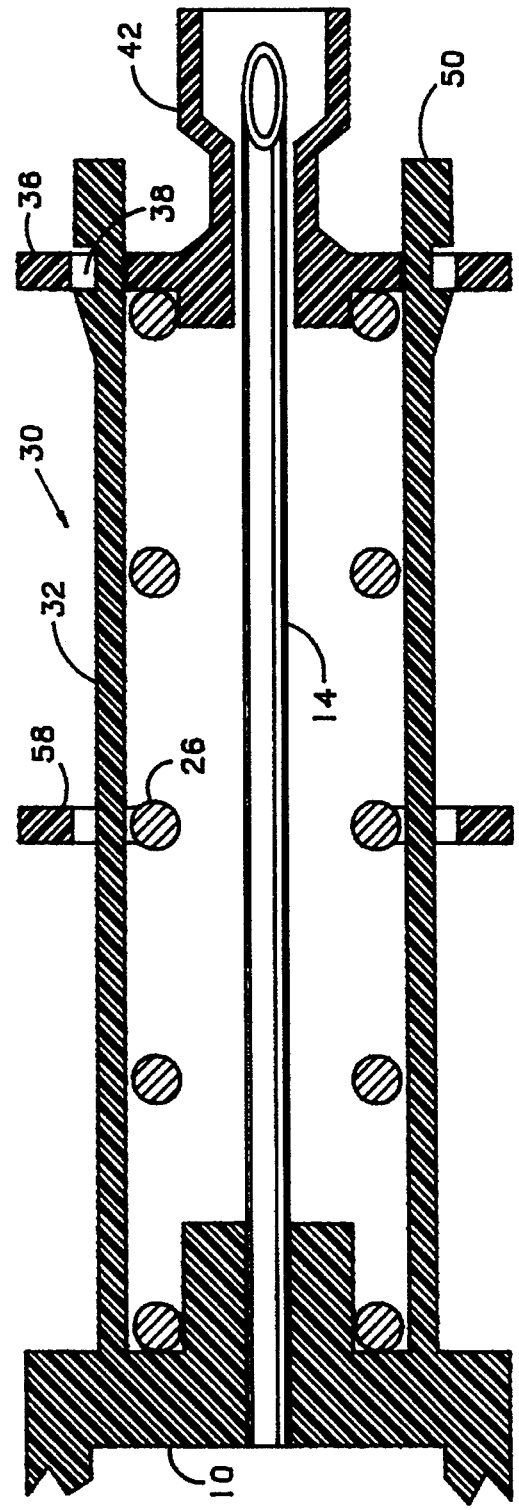

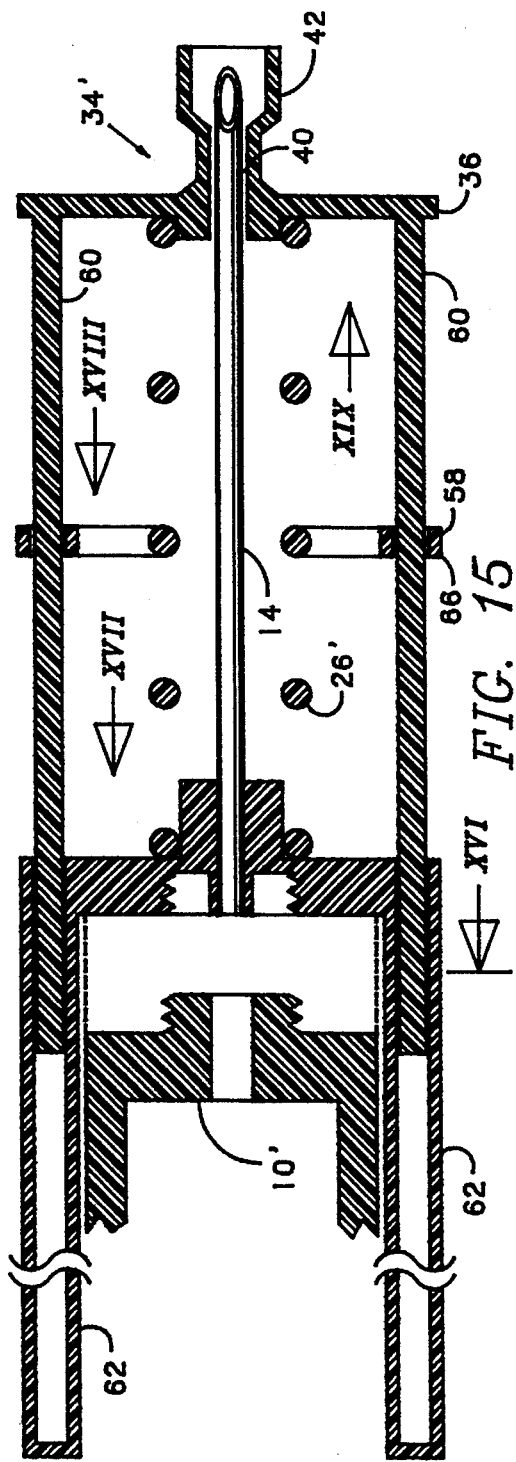
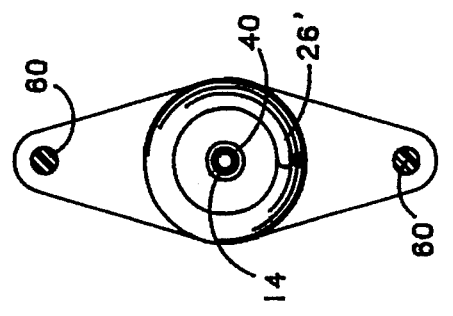
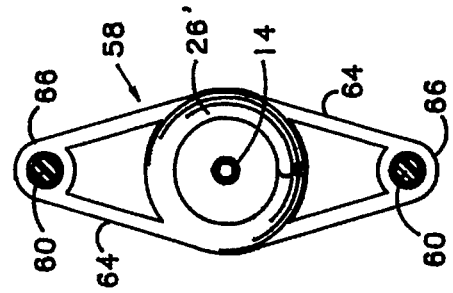
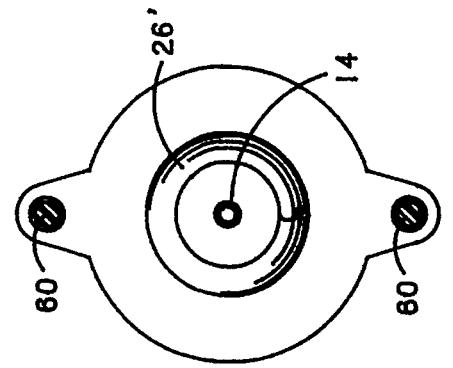
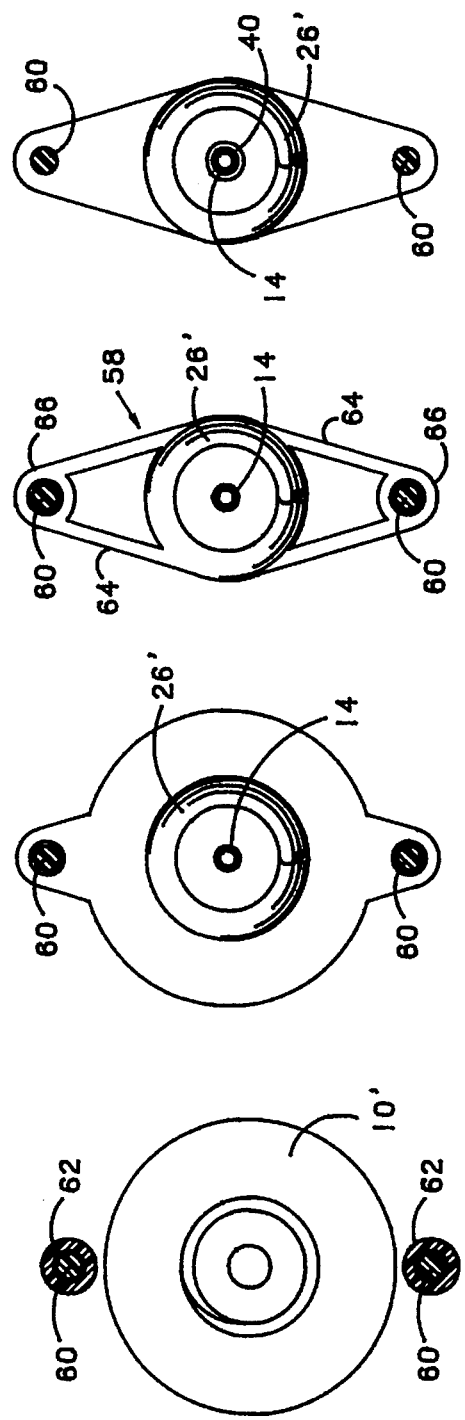

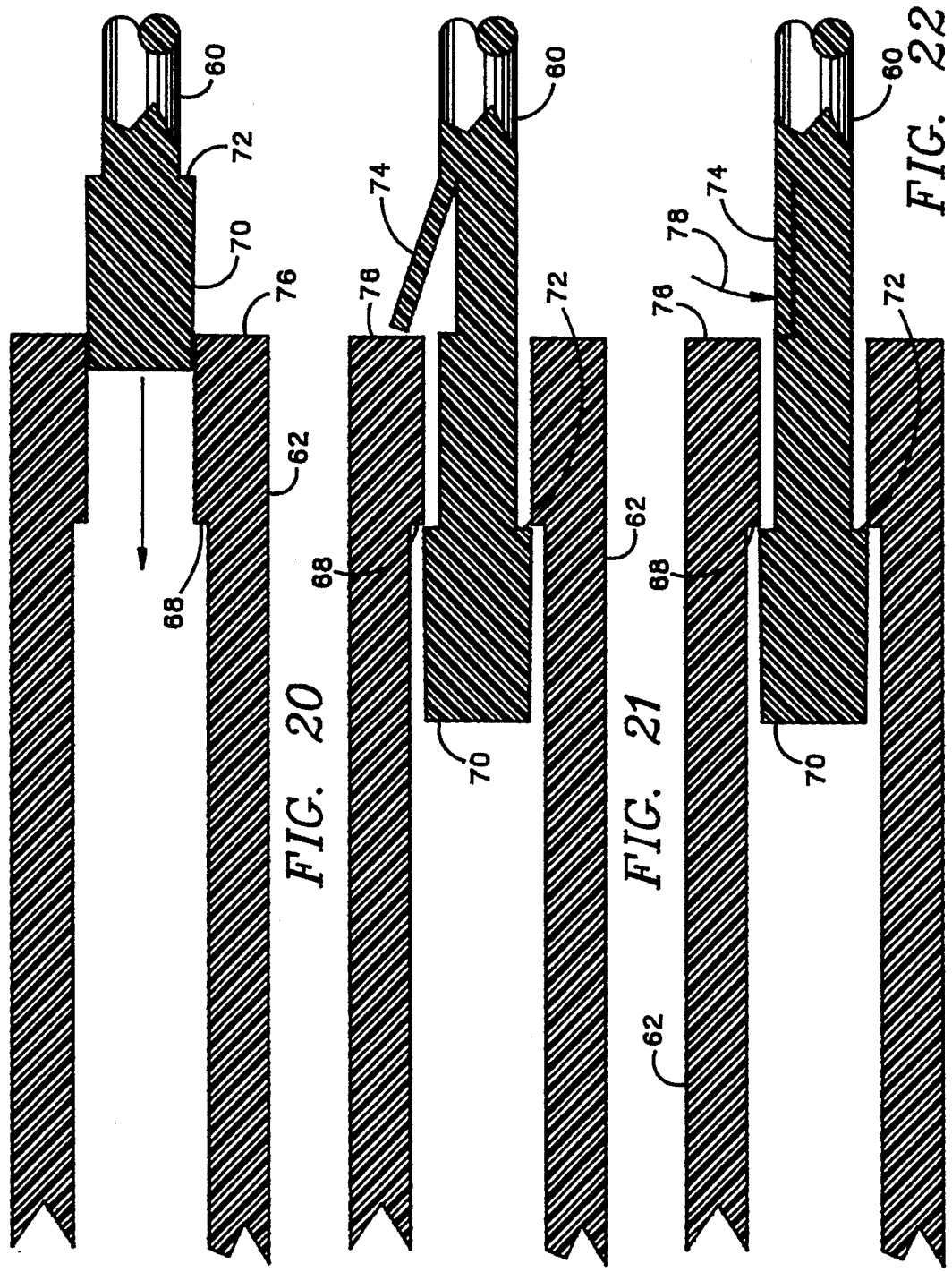

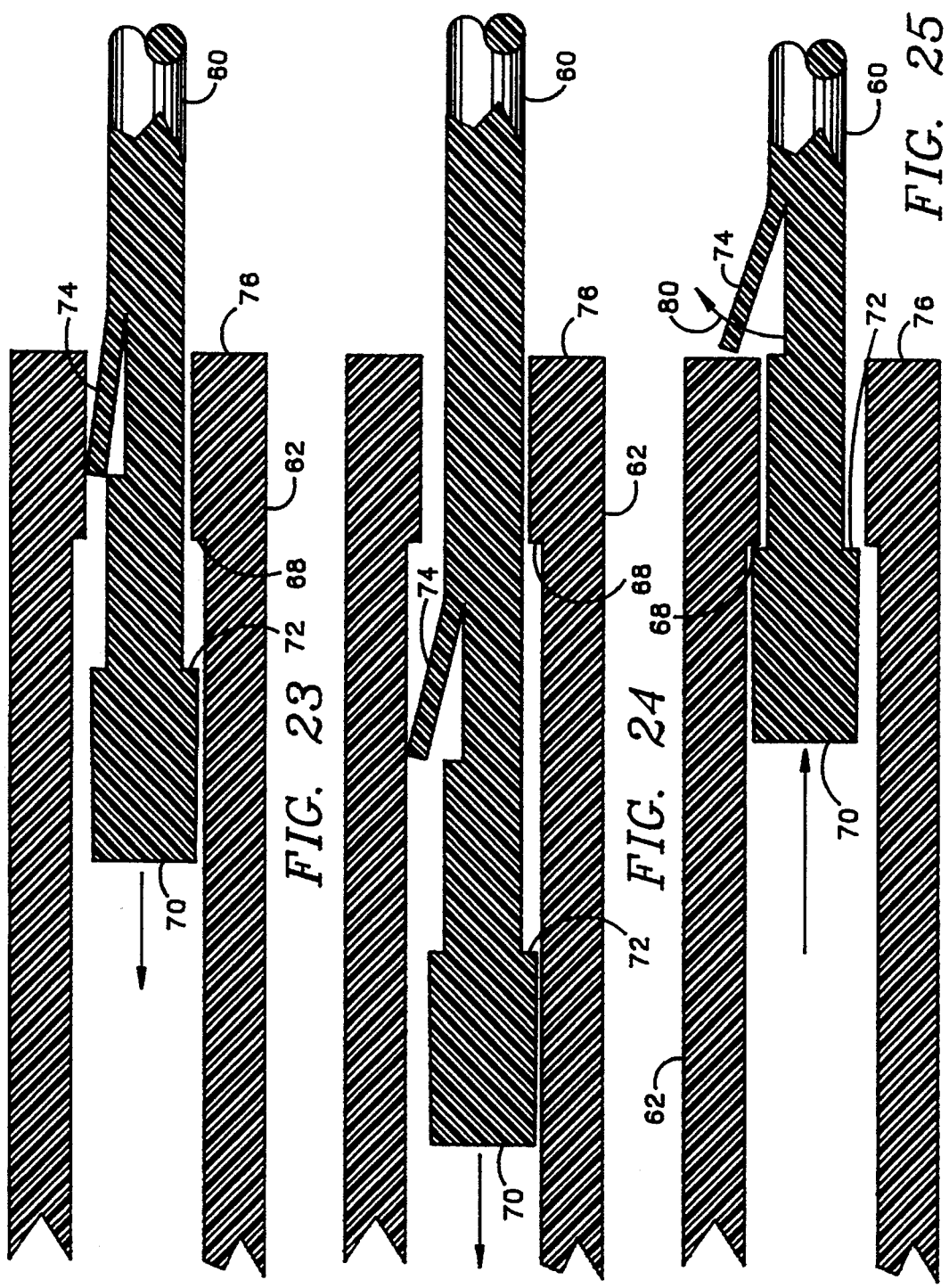

PASSIVE PROTECTOR FOR HYPODERMIC NEEDLES

BACKGROUND OF THE INVENTION

The present invention relates to ways of adding protection against accidental needle-stick to hypodermic syringes and, more particularly, to apparatus for providing passive protection against accidental needle-stick for a hypodermic needle extending from a hub comprising, a tip protector comprising a cross-piece disposed transverse to the needle having an elongated first bore therethrough through which the needle passes and having a bell-shaped tip-guard extending from the cross-piece concentrically about the first bore and covering a tip portion of the needle with the tip protector in an extended position, the tip protector being slidably moveable along the needle supported by the elongated first bore between the extended position and a retracted position with the tip portion of the needle exposed for use; guide means for guiding the tip protector between the extended position and the retracted position; spring means biasing the tip protector to the extended position; and, releasable locking means for automatically releasably locking the tip protector in the extended position when the tip protector moves to the extended position from a position retracted therefrom.

A standard hypodermic syringe 10 as depicted in FIG. 1 has a cylindrical body 12 with a needle 14 extending from one closed end and a sliding plunger 16 extending from an opposite open end. Accidental needle-stick by medical workers has always been an annoyance an a minor medical risk that went with the job. Current statistics say that about 2,700 medical workers get stuck with used needles every day. With contemporary problems such as HIV/AIDS and Hepatitis-B, however, accidental needle-stick has become more than a mere annoyance and minor medical risk. The fear and long uncertainty about having contracted the HIV virus from an accidental needle-stick alone has turned this phenomenon into a national medical crisis.

While there have long been many inventions known in the art for avoiding or at least minimizing the chances of accidental needle-stick, most of them have problems that have prevented their general acceptance at this time. When syringes were reused following autoclaving, initial cost was not a factor and expensive syringes with retractable needles, and the like, could have been successful. With the advent of plastics, however, the disposable syringe became practical thereby eliminating the need for costly and time-consuming autoclaving equipment and processes. Where a standard, unprotected syringe as in FIG. 1 sells in bulk for six cents, a protected version must sell for less than a dollar to be competitive and commercially successful. Several needle protectors have recently been introduced which seek to provide a simple and low-cost solution to the needle-stick problem.

The version of Thomas Kuracina which is the subject of U.S. Pat. No. 4,998,922 is depicted in FIG. 2. There is a protective sleeve 18 comprised of a plurality of longitudinal slats 20 terminating in an end-bell 22. A spring-biased locking collar 24 is positioned over the sleeve 18. By retracting the locking collar 24 against the force of the spring 26, the end-bell 22 can be retracted to expose the needle 14 for use. As the end-bell 22 retracts, the slats 20 bend to the ghosted position shown. When a retracting force on the end-bell 22 is removed (as by withdrawing the needle 14), the self-biasing force of the plastic of the slats 20 moves the end-bell 22 to its extended position covering and protecting the tip of the needle 14. As soon as the slats 20 resume their cylindrical extended shape, the locking collar 24 is pushed forward by the spring 26 thus locking the slats 20 against rebending and the end-bell 22 from retracting. As can be realized from the foregoing description, the Kuracina device is a passive device in that the needle tip is automatically covered when the needle is withdrawn without any action being required on the part of the user. By contrast, a prior art active protective device is shown in FIG. 3. In this case, there is a hard, cylindrical, plastic sleeve 28 slidingly mounted over the body 12 of the syringe 10. For use, the sleeve 28 is retracted as shown to expose the needle 14. After use, the sleeve 28 is manually slid to the ghosted position where it snaps and locks in place.

Since most accidental needle sticks are of the "oops" variety taking place, before the user even has a chance to take any affirmative action to cover the needle as with the sleeve 28 of FIG. 3, passive protective devices are preferred.

In U.K. published Patent Application number GB 2-202-747 A of Dr. William Ducat, a passive hard sleeve protective device as depicted in FIG. 4 is disclosed. The hard sleeve 28 is biased by the spring 26 towards its extended position as shown. An L-shaped locking channel (not shown) on the outer surface of the syringe body 12 interacts with a pin (not shown) on the inner surface of the sleeve 28 to provide an automatic locking action for the sleeve 28. To release the sleeve 28 so that it can be retracted, the sleeve 28 is manually twisted against the torque of the spring 26. When the needle is withdrawn and the sleeve 28 moves forward, when the pin reaches the cross-piece of the "L", the torque of the spring 26 moves the pin into the cross-piece automatically locking the sleeve 28 from further retraction unless and until it is manually twisted again. Obviously, a permanent locking arrangement as employed with the sleeve 28 of FIG. 3 could be added such that after the syringe 10 of FIG. 4 was used and the sleeve 28 was in its releasable locked position, further sliding it forward would cause the permanent lock to set so that the syringe 10 could not be used further. With or without the permanent lock, a hard-sleeve based protective system will generally withstand more longitudinal force without exposing the needle tip than a bendable slat-based system such as that of FIG. 2.

The problem with the spring-biased sleeve of FIG. 4 is that the sleeve 28 moves back over the body 12 of the syringe 10. In the version of FIG. 3, that is not a problem because the syringe 10 is gripped over the retracted sleeve 28 for use and then the sleeve 28 is manually extended. Where automatic (i.e. passive) extension is desired, gripping the syringe 10 by means of the sleeve 28 will interfere with the automatic action of the sleeve 28. Thus, unless special care is taken, the passive protective action may be defeated. Generally, medical workers do not want to use anything that requires deviation from their normal procedure. This could explain from at least one point of view why Dr. Ducat's needle protector is not in general use. Also, this apparatus requires that the syringe body 12 be modified so as to provide the L-shaped locking slot therein. In general, apparatus that can be used with standard components is preferred from both the manufacturing and user point of view. For example, while the Kuracina apparatus of FIG. 2 is pictured built into a unitary syringe, it can be made with the needle 14 and sleeve 18 assembly attached to a standard threaded hub which attaches to a standard syringe body 12 made for such purposes.

Wherefore, it is an object of this invention to provide a passive needle protector for syringes which provides a high degree of longitudinal force resistance like a hard-sleeve system.

It is another object of this invention to provide a passive needle protector for syringes which operates on a sliding sleeve type of approach while not interfering with normal operation of the syringe.

It is still another object of this invention to provide a passive needle protector for syringes which operates on a sliding sleeve type of approach while not requiring any modification to the syringe.

Other objects and benefits of this invention will become apparent to those skilled in the art from the detailed description which follows hereinafter when taken in conjunction with the drawing figures which accompany it.

SUMMARY

The foregoing objects have been achieved by the apparatus of the present invention for providing passive protection against accidental needle-stick for a hypodermic needle extending from a hub comprising, a tip protector comprising a cross-piece disposed transverse to the needle having an elongated first bore therethrough through which the needle passes and having a bell-shaped tip-guard extending from the cross-piece concentrically about the first bore and covering a tip portion of the needle with the tip protector in an extended position, the tip protector being slidably moveable along the needle supported by the elongated first bore between the extended position and a retracted position with the tip portion of the needle exposed for use; guide means for guiding the tip protector between the extended position and the retracted position; spring means biasing the tip protector to the extended position; and, releasable locking means for automatically releasably locking the tip protector in the extended position when the tip protector moves to the extended position from a position retracted therefrom.

In a first embodiment, the guide means comprises a pair of guide rails extending from the hub towards the tip protector and parallel to the needle and a pair of second bores through the cross-piece having respective ones of the pair of guide rails passing therethrough.

In the first embodiment, the locking means may comprises, the pair of second bores each being elongated along a line passing through the needle and having a locking lip at an edge outward from the needle; the pair of guide rails each being self-biased in a direction outward from the needle; and, the pair of guide rails each having a ramped locking tooth and an end-stop on an outward end thereof positioned so that the cross-piece fits between the locking tooth and the end-stop with the locking lip engaged with a non-ramped portion of the locking tooth when the tip protector is in the extended position and locked whereby the tip protector is unlocked for retraction by squeezing the outward ends of the pair of guide rails towards one another.

Preferably there is also support ring means carried by the spring means having a pair of third bores therethrough through which the guide rails pass for supporting the guide rails against outward bowing to increase resistance of the tip protector to longitudinal retracting forces thereon.

In a second embodiment, the guide means comprises a pair of guide tubes extending from the hub away from the tip protector and parallel to the needle and a pair of support rails carried by the cross-piece towards the pair of guide tubes and parallel to the needle, the pair of support rails being sideably disposed within respective ones of the pair of guide tubes.

In this embodiment, the locking means may comprises the pair of guide tubes each having an internal shoulder adjacent an open end thereof through which an associated support rail is inserted; the pair of support rails each having an enlarged end forming an external shoulder inserted through the open end with the internal shoulder abutting the external shoulder with the tip protector in the extended position whereby the bulb end will not easily pass through the open end; and, the pair of support rails each having an outwardly biased locking finger in an outward side thereof spaced back from the enlarged end so that the locking finger abuts an end of an associated one of the pair of guide tubes with the tip protector in the extended position and the tip protector can be unlocked for retraction by squeezing the locking finger of both the pair of support rails against the outward side whereby the locking fingers slide through respective open ends and into the pair of guide tubes.

This embodiment also preferably includes support ring means carried by the spring means having a pair of third bores therethrough through which the support rails pass for supporting the support rails against outward bowing to increase resistance of the tip protector to longitudinal retracting forces thereon.

In either embodiment the hub may be part of the endwall of the body of a hypodermic syringe and a portion of the apparatus for providing passive protection against accidental needle-stick may be formed into the body.

Similarly, in either embodiment the hub may be part of the apparatus for providing passive protection against accidental needle-stick and the entirety of the apparatus may be threadedly attached to the endwall of the body of a hypodermic syringe.

For added protection during shipment and after use, there is a removeable locking bar preferably of styrofoam plastic or the like for preventing said tip protector from moving from said extended position towards said retracted position. The locking bar may also include a portion encasing the tip protector.

DESCRIPTION OF THE DRAWINGS

FIG. 1 is a simplified cutaway drawing of a prior art hypodermic syringe having no protection for the needle.

FIG. 2 is a simplified cutaway drawing of a prior art hypodermic syringe having passive protection for the needle in the form of bendable slats with a locking collar.

FIG. 3 is a simplified cutaway drawing of a prior art hypodermic syringe having active protection for the needle in the form of a lockable sliding sleeve.

FIG. 4 is a simplified cutaway drawing of a prior art hypodermic syringe having passive protection for the needle in the form of a spring-biased, locking, sliding sleeve.

FIG. 5 is a simplified cutaway drawing of a hypodermic syringe having passive protection for the needle according to a first embodiment of the present invention with the tip protector in its extended position.

FIG. 6 is a simplified cutaway drawing of the protected hypodermic syringe of FIG. 5 with the tip protector in its retracted position.

FIG. 7 is a cutaway drawing of FIG. 6 in the plane VII—VII.

FIG. 8 is an enlarged cutaway drawing of the front end of the protected hypodermic syringe of FIGS. 5 and 6 with the tip protector partially retracted, the needle under a patient's skin, and the guide rails riding up over the patient's skin.

FIG. 9 is a greatly enlarged cutaway drawing of the front end of the protected hypodermic syringe of FIGS. 5 and 6 showing the manner of incorporating a locking mechanism therein with the locking mechanism in its locked position FIG. 10 is a greatly enlarged cutaway drawing of the front end of the protected hypodermic syringe of FIGS. 5 and 6 showing the locking mechanism in its unlocked position FIG. 11 is a greatly enlarged cutaway drawing of the front end of the protected hypodermic syringe of FIGS. 5 and 6 showing the sliding protective cap retracted and the guide rails in their self-bias position.

FIG. 12 is a cutaway view of the top portion of the sliding protective cap along the line XII in FIG. 11.

FIG. 13 is a greatly enlarged cutaway drawing of the front end of the embodiment of the present invention of FIGS. 5 and 6 showing how it can be implemented as a screw-on needle for a standard syringe body.

FIG. 14 is a greatly enlarged cutaway drawing of the front end of the embodiment of the present invention of FIGS. 5 and 6 showing an improvement to the spring for supporting the guide rails to increase the longitudinal force the protective cap can resist.

FIG. 15 is a greatly enlarged cutaway drawing of the front end of a syringe employing a screw-on version of a second embodiment of the present invention.

FIG. 16 is an end view of the embodiment of FIG. 15 as viewed from XVI.

FIG. 17 is an end view of the embodiment of FIG. 15 as viewed from XVII.

FIG. 18 is an end view of the embodiment of FIG. 15 as viewed from XVIII.

FIG. 19 is an end view of the embodiment of FIG. 15 as viewed from XIX.

FIG. 20 is a greatly enlarged, cutaway drawing of the support rail and guide tube of the embodiment of FIG. 15 showing one possible way of constructing the locking mechanism depicted in the process of initial assembly.

FIG. 21 is a greatly enlarged, cutaway drawing of the support rail and guide tube of the embodiment of FIG. 15 after initial assembly and showing the locking mechanism in its extended and locked position.

FIG. 22 is a greatly enlarged cutaway drawing of the support rail and guide tube of the embodiment of FIG. 15 after initial assembly showing the locking mechanism in its extended and unlocked position.

FIG. 23 is a greatly enlarged cutaway drawing of the support rail and guide tube of the embodiment of FIG. 15 after initial assembly showing the locking mechanism unlocked and with the support rail in the process of being retracted.

FIG. 24 is a greatly enlarged, cutaway drawing of the support rail and guide tube of the embodiment of FIG. 15 after initial assembly showing the support rail retracting within the guide tube.

FIG. 25 is a greatly enlarged, cutaway drawing of the support rail and guide tube of the embodiment of FIG. 15 after initial assembly showing the support rail extending and relocking after use.

DESCRIPTION OF THE PREFERRED EMBODIMENT

Figure 26:
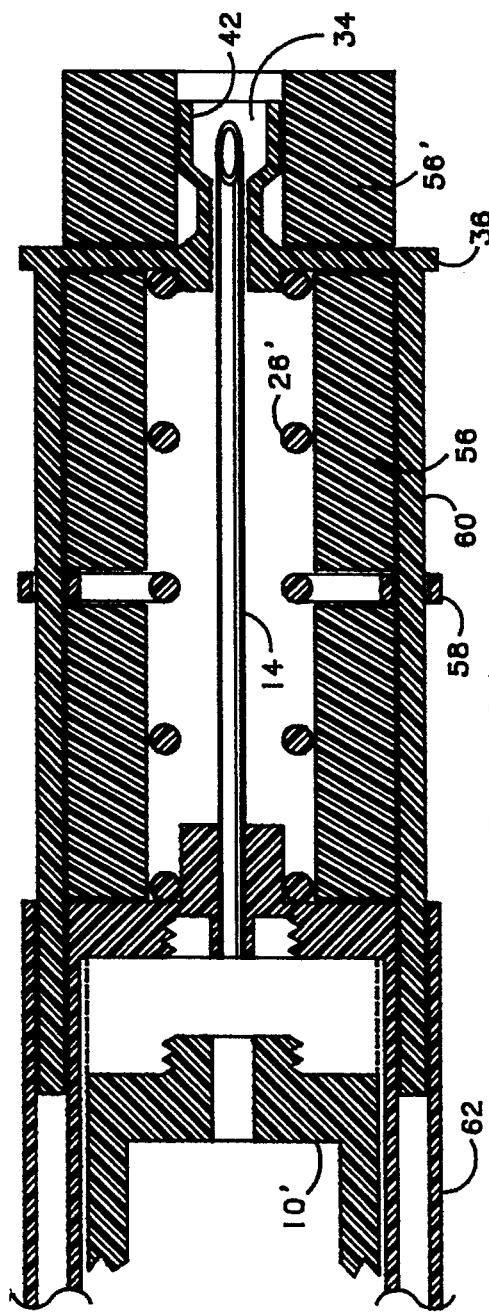
FIG. 26 is a cutaway top view of the present invention with an optional styrofoam-plastic locking bar in place.

The protective apparatus 30 of the present invention is shown in simplified form in a first embodiment in FIGS. 5–7. In this embodiment, there are a pair of parallel guide rails 32 extending outward from the syringe body 12 on opposite sides and generally parallel to the needle 14. A tip protector 34 is slidingly mounted on the guide rails 32 for movement between an extended position as shown in FIG. 5 and a retracted position as shown in FIG. 6. The tip protector 34 is preferably injection molded of plastic and comprises a cross-piece 36 having a pair of bores 38 on opposite sides of an central bore 40. A bell-shaped tip-guard 42 extends from the cross-piece 36 concentrically about the central bore 40 thereby elongating the central bore 40. The needle 14 passes through the elongated central bore 40 and tip-guard 42 while the guide rails 32 pass through respective ones of the bores 38. As depicted in FIGS. 5 and 6, it is preferred that the guide rails 32 be positioned on the sides of the needle 14 (rather than on the top and bottom) so that the needle 14 is visible between them. Additionally, as depicted in FIG. 8, when the needle 14 is inserted under the patient's skin 44 with the tip protector 34 retracted from its extended position of FIG. 5, the forwardly extending portions of the guide rails 32 (also being of plastic) are free to flex and ride up over the patient's skin 44 and not interfere with the injection process. For this purpose and to aid in the locking process to be described hereinafter, it is preferred that the guide rails 32 be self-biased towards an outer position as depicted in FIG. 8. A coil spring 26 disposed within the guide rails 32 and concentrically about the needle 14 between the syringe body 12 and the cross-piece 36 biases the tip protector 34 to its extended position. With the foregoing construction, as the tip protector 34 moves between its extended and retracted positions as depicted in FIGS. 5 and 6, respectively, the elongated bore 40 slides along the needle 14 and supports the tip protector 34 while the guide rails 32 additionally guide the movement of the tip protector 34. The elongated bore 40 also aids in maintaining the tip guard 42 close around the tip of the needle 14 when the tip protector 34 is in its extended position providing much better protection and a more localized skin contact area for applying a retracting force in the manner of the end-bell 22 of the apparatus of FIG. 2 as compared with the sliding sleeve apparatus of FIGS. 3 and 4.

For purposes of simplicity in showing and describing the action of the foregoing embodiment of the present invention, FIGS. 5–8 do not show a locking mechanism for automatically locking the tip protector 34 in its extended position as required to make this an effective passive protective device. One way in which a locking mechanism can be added to the basic components as described is depicted in the enlarged drawings of FIGS. 9–12.

For locking purposes, the bores 38 are generally D-shaped as depicted in FIG. 12 and have an outer locking lip 46. The outer ends of the guide rails 32 each have a ramped locking tooth 48 and an end-stop 50 spaced therefrom. The depth of the bore 38 from the locking lip 46 is sufficient that the locking tooth 48 can clear the locking lip 46 when the ends of the guide rails 32 are pressed inwardly as depicted in FIG. 10. The guide rails 32 are self-biased to an outward position as depicted in FIG. 11. With the tip protector 34 in its initial extended position as depicted in FIG. 9, the guide rails 32 are squeezed inward by the locking lips 46. Thus, the locking lips 46 are each forced into the space between the locking tooth 48 and end-stop 50 where the tip protector 34 is held against either forward or backward movement.

To unlock and retract the tip protector 34 for use, the user merely squeezes the tips of the guide rails 32 inward as indicated by the arrows 52 while simultaneously pulling backward on the ends of the cross-piece 36 as indicated by the arrows 54. This should be a one-handed operation performed by pinching and pulling with the thumb and fore-finger. As soon as the needle 14 is inserted, the tip protector 34 can be released to assume the position of FIG. 8 so that the tip protector 34 will automatically move towards the forward and locked position of FIG. 9 as the needle 14 is withdrawn from the patient (or comes out for any reason).

Several possible modifications or additions to the above-described embodiment are shown in FIGS. 13 and 14. FIG. 13 shows how the foregoing embodiment could be configured as a screw-on assembly for a standard screw-front syringe 10'. FIG. 14 depicts a support ring 58 having the guide rails 32 passing therethrough carried by a central portion of the spring 26 to prevent the guide rails 32 from bowing out so as to add further longitudinal force resistance. This will be readdressed in further detail in the following embodiment.

A second embodiment of the present invention configured as a screw-on assembly for a standard screw-front syringe 10' is depicted in FIGS. 15–19. In this embodiment, the tip protector 34' carries a pair of spaced support rails 60 extending backwards therefrom. The support rails 60 slidingly fit within a pair of guide tubes 62 carried on opposite sides of the syringe body 12. In a unitary implementation, the guide tubes 62 could be formed into the outer sidewalls of the body 12. In this embodiment, the spring 26' is shown being formed of plastic (whereas the first embodiment showed a spring cross-hatched for metal) with the support ring 58 integrally molded into the structure of the spring 26' at a central portion thereof. As best seen in FIG. 18, the support ring 58 comprises arms 64 extending radially outward from the spring 26' and carrying a pair of 180° spaced annular members 66 through which respective ones of the support rails 60 pass. While the support rails 60 are shown as round in cross-section as were the guide rails 32 of the prior embodiment, those skilled in the art will readily recognize and appreciate that they could be of different cross-sectional shape if desired and, in fact, a more oval shape up and down might be desirable to provide additional compressive force resistance. As in the prior embodiment, it is preferred that the support rails straddle the needle 14 on its sides to make the needle more easily viewable. Note that in this embodiment, the support rails 60 move out of the way altogether as compared with the prior embodiment in which they remained in the area of the needle insertion and merely moved out of the way.

As with the prior embodiment, the basic concept as described above was done without the inclusion of a locking mechanism for the tip protector 34'. One possible approach to a locking mechanism is depicted in the greatly enlarged drawings of FIGS. 20–25. The guide tubes 62 have a smaller diameter at their open end facing the tip protector 34 thereby forming a shoulder 68. The support rails 60 have an enlarged diameter at their free ends thereby forming an enlarged bulb end 70 terminating in a shoulder 72. For ease of assembly, the bulb end 70 can be somewhat tapered. The outside diameter at the shoulder 72 is substantially identical to the inside diameter of the shoulder 68. As depicted in FIGS. 20 and 21, initial assembly of the support rails 60 into the guide tubes 62 is done by forcing the bulb ends 70 through and past respective ones of the shoulders 68. Once inside, the bulb ends 70 can slide freely within the guide tubes 62 but cannot easily come out as the shoulders 68, 72 tend to offset and abut one another.

An outwardly biased locking finger 74 is formed in the side of each support rail behind the bulb end 70 as depicted in FIG. 21. In the extended and locked position as shown therein, the shoulders 68, 72 are in abutment and the locking finger 74 is close adjacent being in contact with the end 76 of the guide tube 62. Thus, the support rails 60 are prevented from moving either forward or backward.

To retract the tip protector for use, the locking fingers 74 are squeezed against the support rails 60 as indicated by the arrow 78 in FIG. 22. The support rails 60 can then move into the guide tubes 62 as depicted in FIGS. 23 and 24 so that the tip protector 34' cart move to a retracted position against the force of the spring 26'. When the retracting force on the tip protector 34' is removed, the support rails 60 move forward within the guide tubes until the forward and locked position of FIG. 25 is reached when the shoulders 68, 72 are once again in abutment and the locking fingers 74 are free to spring outward to their locking position from the self-biasing force of the plastic as depicted by the arrow 80 in FIG. 25.

Figure 28:
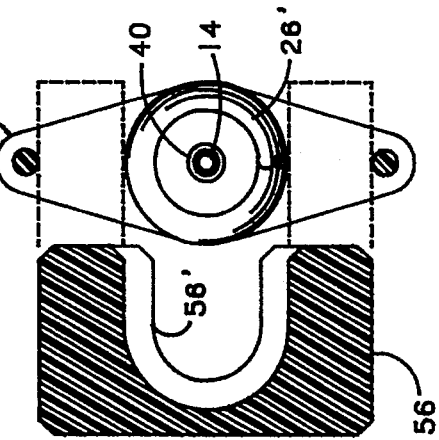
FIG. 28 is a cutaway end view through the locking bar of FIG. 27 showing how it is inserted.
Figure 27:
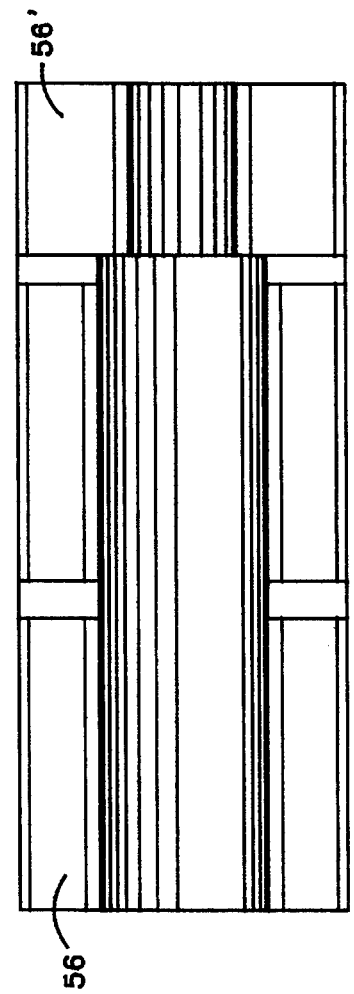
FIG. 27 is a drawing of the locking bar looking into the C-shape thereof.

As shown in FIGS. 26–28, a plastic locking bar 56 C-shaped in cross section could be pressed between the guide rails 32 of the first embodiment or between the support rails 60 of the second embodiment preferably for all of the length thereof to prevent the tip protector 34 from being retracted after use and/or during shipment thereby increasing the resistance to a longitudinal force. For maximum protection, it could include a portion 56' in front of the cross-piece 36 which receives the tip-guard 42. It is anticipated that use of a styrofoam plastic for the plastic locking bar 56 would provide a very high degree of protection at a very, low price as styrofoam is extremely lightweight and highly crush-resistant under the forces that might be encountered.

As those skilled in the art will undoubtedly recognize and appreciate, the foregoing two embodiments of the present invention are not limited to use with syringes. By adapting the self-contained versions intended to screw onto a syringe, needles for catheters, and the, like, can be protected in a like manner.

Wherefore, having thus described the present invention, what is claimed is:

1. Apparatus for providing passive protection against accidental needle-stick for a hypodermic needle extending from a hub comprising:

a) a tip protector comprising a cross-piece disposed transverse to the needle having an elongated first bore therethrough through which the needle passes and having a bell-shaped tip-guard extending from the cross-piece concentrically about said first bore and covering a tip portion of the needle with said tip protector in an extended position, said tip protector being slidably moveable along the needle supported by said elongated first bore between said extended position and a retracted position with said tip portion exposed for use, said first bore being close adjacent and behind said tip portion when in said extended position and behind and removed from said tip portion when in said retracted position;

b) guide means for guiding said tip protector between said extended position and said retracted position, said guide means comprising, b1) a pair of guide tubes extending from the hub away from said tip protector and parallel to the needle, and b2) a pair of support rails integrally formed as part of and extending from said cross-piece towards said pair of guide tubes and parallel to the needle, said pair of support rails being slidably disposed within respective ones of said pair of guide tubes;

c) a helical spring concentrically disposed about the needle between the hub and said cross piece biasing said tip protector to said extended position; and, d) releasable locking means for automatically releasably locking said tip protector in said extended position when said tip protector moves to said extended position from a position retracted therefrom.

2. The apparatus for providing passive protection against accidental needle-stick for a hypodermic needle of claim 1 wherein said locking means comprises:

a) said pair of guide tubes each having an internal shoulder adjacent an open end thereof through which an associated said support rail is inserted;

b) said pair of support rails each having an enlarged end forming an external shoulder inserted through said open end with said internal shoulder abutting said external shoulder with said tip protector in said extended position whereby said bulb end will not easily pass through said open end; and, c) said pair of support rails each having an outwardly biased locking finger in an outward side thereof spaced back from said enlarged end so that said locking finger abuts an end of an associated one of said pair of guide tubes with said tip protector in said extended position and said tip protector can be unlocked for retraction by squeezing said locking finger of both said pair of support rails against said outward side whereby the locking fingers slide through respective open ends and into said pair of guide tubes.

3. The apparatus for providing passive protection against accidental needle-stick for a hypodermic needle of claim 1 and additionally comprising:

support ring means carried by said helical spring having a pair of third bores therethrough through which said support rails pass for supporting said support rails against outward bowing to increase resistance of said tip protector to longitudinal retracting forces thereon.

4. Apparatus for providing passive protection against accidental needle-stick for a hypodermic needle extending from a hub comprising:

a) a tip protector comprising a cross-piece disposed transverse to the needle having an elongated first bore therethrough through which the needle, passes and having a bell-shaped tip-guard extending from the cross-piece concentrically about said first bore and covering a tip portion of the needle with said tip protector in an extended position, said tip protector being slidably moveable along the needle supported by said elongated first bore between said extended position and retracted position with said tip portion of the needle exposed for use, said first bore being close adjacent and behind said tip portion When in Said extended position and behind and removed from said tip portion when in said retracted position;

b) guide means for guiding said tip protector between said extended position and said retracted position, said guide means comprising, b1) a pair of guide tubes extending from the hub away from said tip protector and parallel to the needle, and b2) a pair of support rails carried by said cross-piece towards said pair of guide tubes and parallel to the needle, said pair of support rails being slidably disposed within respective ones of said pair of guide tubes;

c) spring means concentrically disposed about the needle for biasing said tip protector to said extended position; and, d) releasable locking means for automatically releasably locking said tip protector in said extended position when said tip protector moves to said extended position from a position retracted therefrom.

5. The apparatus for providing passive protection against accidental needle-stick for a hypodermic needle of claim 4 wherein said locking means comprises:

a) said pair of guide tubes each having an internal shoulder adjacent an open end thereof through which an associated said support rail is inserted;

b) said pair of support rails each having an enlarged end forming an external shoulder inserted through said open end with said internal shoulder abutting said external shoulder with said tip protector in said extended position whereby said bulb end will not easily pass through said open end; and, c) said pair of support rails each having an outwardly biased locking finger in an outward side thereof spaced back from said enlarged end so that said locking finger abuts an end of an associated one of said pair of guide tubes with said tip protector in said extended position and said tip protector can be unlocked for retraction by squeezing said locking finger of both said pair of support rails against said outward side whereby the locking fingers slide through respective open ends and into said pair of guide tubes.

6. The apparatus for providing passive protection against accidental needle-stick for a hypodermic needle of claim 4 and additionally comprising:

support ring means carried by said spring means having a pair of third bores therethrough through which said support rails pass for supporting said support rails against outward bowing to increase resistance of said tip protector to longitudinal retracting forces thereon.

7. The apparatus for providing passive protection against accidental needle-stick for a hypodermic needle of claim 4 wherein:

a) the hub is part of an endwall of a body of a hypodermic syringe; and, b) sale guide tubes are formed into outer surfaces of sidewalls of said body.

8. The apparatus for providing passive protection against accidental needle-stick for a hypodermic needle of claim 4 wherein:

a) the hub is part of the apparatus for providing passive protection against accidental needle-stick; and b) the entirety of the apparatus for providing passive protection against accidental needle-stick is threadedly attached to an endwall of a body of a hypodermic syringe.

* * * * *